(12) United States Patent
Guieze et al.

(10) Patent No.: US 6,568,248 B1
(45) Date of Patent: May 27, 2003

(54) METHOD AND APPARATUS FOR THERMODYNAMIC ANALYSIS OF A MIXTURE OF FLUIDS

(75) Inventors: Paul Guieze, Fontenailles (FR); Pierre Le Foll, Antony (FR)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

(21) Appl. No.: 09/936,986

(22) PCT Filed: Mar. 17, 2000

(86) PCT No.: PCT/EP00/02475

§ 371 (c)(1),
(2), (4) Date: Feb. 20, 2002

(87) PCT Pub. No.: WO00/57176

PCT Pub. Date: Sep. 28, 2000

(30) Foreign Application Priority Data

Mar. 23, 1999 (FR) .............................................. 99 03582

(51) Int. Cl.$^7$ .......................... G01N 1/02; G01N 33/22; G01N 33/28; E21B 49/00; E21B 49/08
(52) U.S. Cl. .................... 73/61.78; 73/19.05; 73/24.01; 73/24.06; 73/31.04; 73/64.53
(58) Field of Search ............................. 73/19.05, 24.01, 73/24.06, 31.04, 61.78, 64.53, 61.47

(56) References Cited

FOREIGN PATENT DOCUMENTS

| GB | 2330654 | * | 4/1999 | .................. 73/863 |
| SU | 250808 | * | 8/1967 | ................ 73/61.78 |

* cited by examiner

*Primary Examiner*—Daniel S. Larkin
(74) *Attorney, Agent, or Firm*—Victor H. Segura

(57) ABSTRACT

The invention relates to a method and to apparatus for thermodynamic analysis of a mixture of fluids, in which the volume of a sample of a given quantity of said mixture is caused to vary step by step and in monotonic manner, and the pressure of the sample is read at each step, the sample being stirred at each step so as to hasten the mixture reaching thermodynamic equilibrium. According to the invention, the sample is stirred by applying ultrasound to said sample by means of transducer (20). The sample can be contained in a bag (19) of flexible material immersed together with the transducer in a control fluid inside a rigid container (10). The invention can be used to determine the bubble point of a mixture of hydrocarbons.

8 Claims, 2 Drawing Sheets

METHOD AND APPARATUS FOR THERMODYNAMIC ANALYSIS OF A MIXTURE OF FLUIDS

The present invention relates to a method and to apparatus for thermodynamic analysis of a mixture of fluids, in particular of hydrocarbons.

More particularly, the invention relates to such a method comprising the steps consisting in:

causing the volume of a sample of a given quantity of said mixture to vary step by step in monotonic manner; and reading the pressure of the sample at each step;

in which method the sample is stirred on each step so as to hasten the mixture reaching thermodynamic equilibrium.

A fundamental operation when characterizing the properties of a fluid extracted from a hydrocarbon deposit lies in determining the saturation point of the fluid. It is this saturation point that determines the conditions under which the fluid will be present as a single phase or as a plurality of phases, i.e. whether it will be in the form solely of a gas or of a liquid, or whether it will be in the form of a mixture of gas and of liquid, and it is essential to know these conditions in order to be able to work the deposit.

The saturation point of a fluid at a given temperature is generally defined as being the pressure at which the single phase fluid begins to be present in the form of a plurality of phases.

Thus, the pressure at which a fluid initially contained in the liquid state in a deposit releases a first bubble of gas as its pressure is decreased is known as the "bubble point". Conversely, if the fluid is initially in the gaseous state, and its pressure is decreased, the pressure at which the first drop of liquid forms is called the "dew point".

The saturation point of a given fluid is determined by performing pressure-volume-temperature (PVT) analysis or "thermodynamic" analysis, consisting in observing as a function of time the pressure and the change in the volume of a sample of fluid that is subjected to varying pressure. This operation is preferably performed at constant temperature equal to that of the reservoir from which the fluid under investigation was taken.

For this purpose, the fluid is inserted in the single phase state into a sealed enclosure at high pressure known as a "PVT cell" which can be maintained in stable manner at the desired temperature. Such a cell is made in conventional manner in the form of a chamber subdivided into two portions by a moving piston. The sample of fluid is placed on one side of the piston and a control fluid is placed on the other side.

When determining the bubble point, the pressure in the cell is then decreased in steps by displacing the moving piston by progressively withdrawing control fluid from the portion of the chamber containing it. The sample fluid can thus expand and occupy a larger volume. During this process, the pressure P and the change in volume $\Delta V$ are observed as a function of time t, and a curve of P as a function of $\Delta V$ is plotted.

When the pressure reaches the saturation point, the fluid begins to release the second phase, in this case the gas phase, on the fluid reaching the bubble point. This point is detected by a discontinuity in the slope of the curve $$P = f(\Delta V)$$

FIG. 1 is a plot at constant temperature showing how volume and pressure varied as a function of time (in seconds) during an experiment seeking to determine the bubble point of a mixture of liquid hydrocarbons.

Curve 1 shows the variation in the volume (in $cm^3$) of the sample, and curve 2 shows the variation of its pressure (in MPa). The periods 3 during which the mixture is in thermodynamic equilibrium can be seen clearly in the form of level portions of stable pressure. The periods 4 during which thermodynamic equilibrium is changing can also be seen clearly in this figure.

Figure 2:
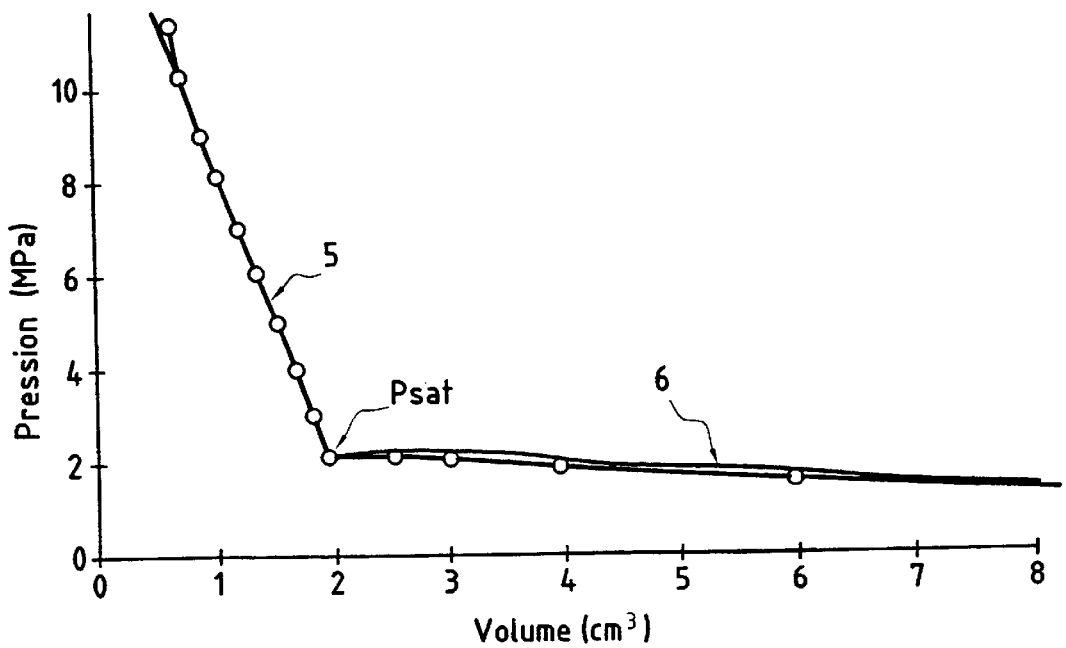

In FIG. 2, the time parameter has been eliminated so that pressure is shown directly as a function of change in volume. This representation is constituted in the present case by two half-curves 5 and 6 in which respectively volume and pressure are relatively constant.

The saturation point (Psat) appears as the point of the FIG. 2 curve where it presents a discontinuity of slope.

Figure 1:
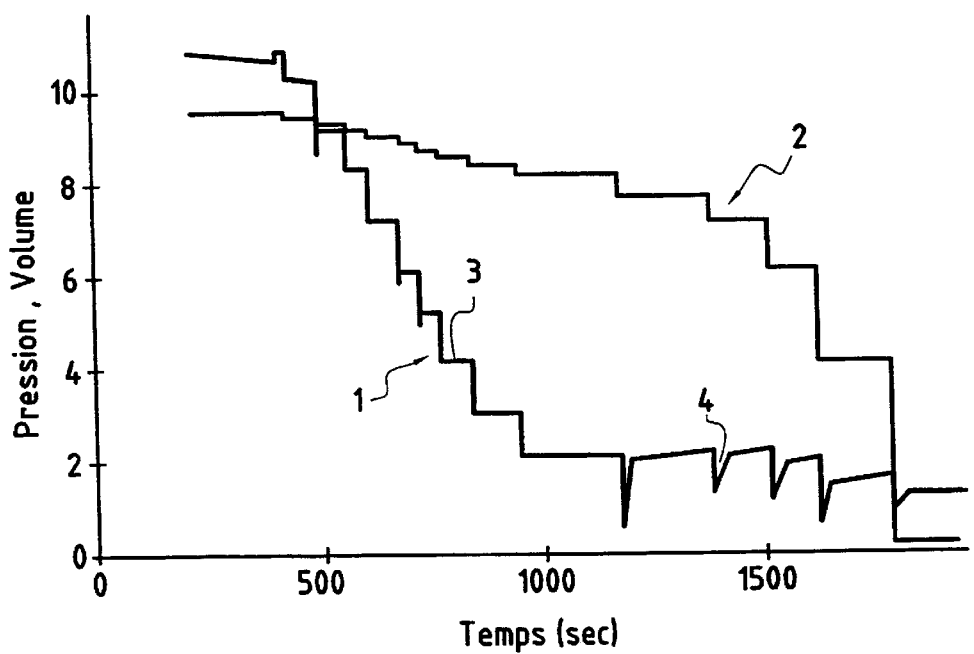
FIGS. 1 and 2 show an example of the method as outlined above.

During the manipulation that leads to the curves of FIGS. 1 and 2, it is necessary at each step to wait for pressure to stabilize (period 4). The accuracy with which the saturation point is determined depends to a very large extent on the quality of the thermodynamic equilibrium.

In order to hasten equilibrium, it is known that the fluid contained in the PVT cell can be stirred. For this purpose, the cell is rotated about an axis and a metal element, such as a bead or a ring, is placed so as to be free to move in the fluid that is to be stirred while the cell is being rotated.

Use has also been made of mercury simultaneously as piston and as stirrer. However, that practice has disappeared because mercury is potentially dangerous for the users implementing the method.

Furthermore, the experiment needs to be repeated several times in order to be sure of the result. It is therefore necessary after the fluid has become dissociated to recombine its two phases by increasing the pressure in the cell beyond the bubble point. In that case also, stirring is necessary in order to hasten recombination.

It is therefore essential for the stirring process to be as effective as possible in order to reduce the time required to reach thermodynamic equilibrium after each step of the experiment. Unfortunately, the known methods mentioned above are of relatively limited effectiveness, only.

The present invention seeks to mitigate that drawback.

More particularly, an object of the invention is to provide a method and apparatus for determining the saturation point of a fluid mixture while reducing the time required for the experiment, and which is independent of the type of hydrocarbon concerned.

To this end, in a first aspect, the invention provides a method of thermodynamically analyzing a mixture of fluids, in particular of hydrocarbons, the method comprising the steps consisting in:

causing the volume of a sample of a given quantity of said mixture to vary step by step in monotonic manner; and reading the pressure of the sample at each step;

in which method the sample is stirred on each step so as to hasten the mixture reaching thermodynamic equilibrium;

the method being characterized by the fact that the stirring of the sample comprises a step of applying ultrasound to the sample.

It has been found that it is possible to obtain good uniformity of the fluid sample by applying ultrasound thereto. The pressure waves generated in this way assist in bringing the fluid to thermodynamic equilibrium. They avoid metastable equilibrium being established, thus making it possible for the saturation point to be identified with certainty and to be determined with accuracy.

In a first implementation of the method, the ultrasound is applied to a rigid container containing the sample. This applies, for example, when the method is used in a piston device of the type outlined above.

Nevertheless, in another implementation, the ultrasound is applied to a fluid in which a bag of flexible material containing the sample is immersed. This implementation requires a smaller amount of energy.

In a particular implementation, the ultrasound is applied after a succession of steps in which the volume is varied monotonically and during a step in which the direction of volume variation is reversed.

This applies when the measurement is repeated several times and where the pressure therefore needs to be returned to its initial value before beginning a new series of stages in which pressure is varied step by step.

Naturally, the method of the invention can be applied equally well to determining the bubble point of a mixture of fluids in which the pressure of a liquid sample is reduced step by step, or to determining the dew point of a mixture of fluids in which the pressure of a gaseous sample is decreased step by step.

In a second aspect, the invention provides apparatus for determining the saturation point of a mixture of fluids, the apparatus comprising an enclosure suitable for containing a sample of said mixture and means for stirring said sample, the apparatus being characterized by the fact that said stirring means comprises means for generating ultrasound in said sample.

In a first embodiment, said enclosure comprises a rigid container organized to contain directly a sample of said mixture, said means for generating ultrasound being mounted to apply the ultrasound to said container.

In which case, said means for generating ultrasound is disposed on the outside of said container.

In another embodiment, said enclosure comprises a bag of flexible material suitable for containing said sample, said bag being received in a rigid container with a second fluid being interposed between the bag container, said means for generating ultrasound being mounted to apply the ultrasound to said second fluid.

In which case, said means for generating ultrasound is disposed inside said container, immersed in said second fluid.

Figure 3:
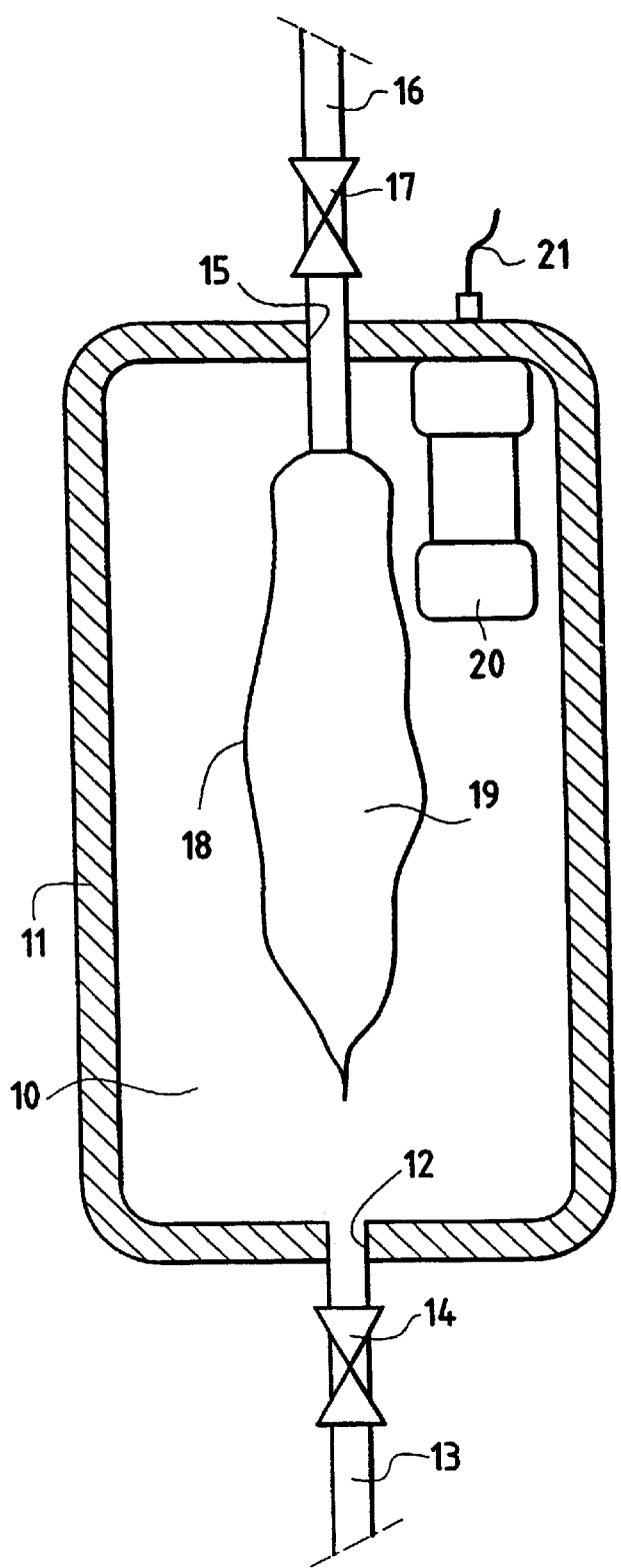

A particular embodiment of the invention is described below by way of non-limiting example and with reference to the accompanying drawings, in which:

FIGS. 1 and 2 show the curves obtained when determining the bubble point of a mixture of liquid hydrocarbons; and FIG. 3 is a diagrammatic section through apparatus of the invention.

FIGS. 1 and 2 are described above. Reference is thus made directly to FIG. 3.

This figure shows an enclosure 10 defined by a rigid wall 11 and fitted with a filling and emptying orifice 12. A duct 13 is connected to the orifice 12 and a valve 14 is mounted on the duct 13 so as to control the admission of fluid into or the withdrawal of fluid from the enclosure 10.

Another orifice 15 is provided in the wall 11 of the enclosure 10. This orifice 15 allows a duct 16 to pass into the enclosure and flow in the duct 16 is controlled by a valve 17.

The duct 16 thus passes through the wall 11 and the end of the duct inside the enclosure 10 is connected to the wall 18 of a bag 19 of flexible material that withstands hydrocarbons and temperature.

In this case, the bag 19 is made by peripheral bonding or heat sealing of two sheets. In practice, the end of the duct 16 inside the enclosure 10 is connected by any appropriate means to an orifice formed in one of the sheets of the bag 19.

The valve 17 allows the sample whose saturation point is to be determined to be admitted into the bag 19. The valve 14 is designed to control the volume of control fluid contained in the enclosure 10 outside the bag 19.

The above device is not described in greater detail insofar as it is itself known from document FR-A-2 754 307. The means for controlling the volume of fluid and the means for measuring said volume and its pressure are of any appropriate type and they are therefore not described in detail either.

By extracting a given volume of control fluid from the enclosure 10 while the valve 17 is open, an equal volume of sample fluid is admitted into the bag 19. After the valve 17 has been closed, pressure in the enclosure 10 is controlled, thereby controlling pressure in the bag 19, by admitting or withdrawing control fluid via the duct 13 and the valve 14.

In accordance with the invention, a piezoelectric transducer 20 is mounted on the wall 11 inside the enclosure 10. This transducer is powered by a cable 21 passing through the wall 11. When powered, it enables ultrasound to be emitted into the control fluid, which ultrasound is transmitted to the sample fluid through the flexible wall of the bag 19. The ultrasound used can have a frequency of about 40 kHz.

The saturation point of the fluid sample contained in the bag 19 is determined in the prior art manner by controlling the volume of control fluid that is admitted into or withdrawn from the enclosure 10, and by monitoring the pressure of the fluid sample contained in the bag 19.

However, the enclosure 10 in this case is fixed, and the fluid sample is stirred in accordance with the invention by emitting a burst of ultrasound into the control fluid by means of the transducer 20.

The above device is described purely by way of example, and the invention can be used with other types of enclosure.

Thus, the fluid sample can be received in a container having rigid walls, of the same type as a prior art piston cell. In which case, the transducer 20 can be mounted on one of said walls outside the container However, the energy required for stirring the fluid would then be considerably greater.

What is claimed is:

1. A method of thermodynamically analyzing a mixture of fluids, the method comprising the steps of:
   introducing a sample of a given quantity of a mixture in a flexible bag;
   causing the volume of the flexible bag to vary step by step in a monotonic manner; and
   reading the pressure of the sample at each step;
   the method being characterised in that the sample is stirred on each step so as to hasten the mixture reaching thermodynamic equilibrium, said stirring comprising applying ultrasound to the sample.

2. A method according to claim 1, in which the ultrasound is applied to a fluid in which a flexible bag (19) containing the sample is immersed.

3. A method according to any one of claims 1 or 2, in which the ultrasound is applied after a succession of steps in which the volume of the flexible bag is varied monotonically and during a step in which the direction of volume variation of the flexible bag is reversed.

4. A method according to claim 1, comprising determining the bubble point of a mixture of fluid by decreasing the pressure of a liquid sample in a step by step manner.

5. A method according to claim 1, comprising determining the dew point of a mixture of fluids by decreasing the pressure of a gas sample in a step by step manner.

6. Apparatus for determining the saturation point of a mixture of fluids, the apparatus comprising a flexible enclosure (19) suitable for containing a sample of said mixture, means to control the volume of said flexible enclosure and means to monitor the pressure of said sample in order to determine the saturation point of said mixture of fluids, the apparatus being characterised in that the apparatus further comprises means for stirring said sample, said stirring means comprising means (20) for generating ultrasound in said sample.

7. Apparatus according to claim 6, in which said enclosure comprises a bag (19) of flexible material suitable for containing said sample, said bag being received in a rigid container (10) with a second fluid being interposed between the bag and the container, said means (20) for generating ultrasound being mounted to apply the ultrasound to said second fluid.

8. Apparatus according to claim 7, in which said means for generating ultrasound is disposed inside said container (10), immersed in said second fluid.

\* \* \* \* \*